US012735447B2

(12) United States Patent
Lenna et al.

(10) Patent No.: US 12,735,447 B2
(45) Date of Patent: Sep. 15, 2026

(54) PROCESS FOR PREPARING B-[(7α, 17β)-17-HYDROXY-7-[9-[(4,4,5,5,5-PENTAFLUOROPENTYL)SULFINYL] NONYL]ESTRA-1,3,5(10)-TRIEN-3-YL]-BORONIC ACID AND PROCESS INTERMEDIATES

(71) Applicant: INDUSTRIALE CHIMICA S.R.L., Milan (IT)

(72) Inventors: Roberto Lenna, S. Giorgio su Legnano (IT); Andrea Fasana, Nesso (IT)

(73) Assignee: Industriale Chimica S.R.L., Milan (IT)

(*) Notice: Subject to any disclaimer, the term of this patent is extended or adjusted under 35 U.S.C. 154(b) by 310 days.

(21) Appl. No.: 18/701,763

(22) PCT Filed: Oct. 29, 2021

(86) PCT No.: PCT/IB2021/060016

§ 371 (c)(1),
(2) Date: Apr. 16, 2024

(87) PCT Pub. No.: WO2023/073413

PCT Pub. Date: May 4, 2023

(65) Prior Publication Data

US 2025/0136637 A1 May 1, 2025

(51) Int. Cl.
*C07J 31/00* (2006.01)

(52) U.S. Cl.
CPC .................................. *C07J 31/006* (2013.01)

(58) Field of Classification Search
None
See application file for complete search history.

(56) References Cited

U.S. PATENT DOCUMENTS

| | | | | |
|---|---|---|---|---|
| 10,112,962 | B2 * | 10/2018 | Wang | A61P 19/02 |
| 2024/0174711 | A1 * | 5/2024 | Lenna | C07J 31/006 |
| 2024/0218013 | A1 * | 7/2024 | Lenna | C07J 31/006 |

OTHER PUBLICATIONS

International Search Report and Written Opinion for International Application No. PCT/IB2021/060016, dated Aug. 5, 2022, 14 pages.

Eve J. Brazier, Philip J. Hogan, et al. Fulvestrant: From the Laboratory to Commercial-Scale Manufacture. Organic Process Research & Development 2010, 14, 544-552.

Jiawang Liu et al, Fulvestrant-3 boronic acid (ZB716): an orally bioavailable selective estrogen receptor downregulator (SERD). J. Med. Chem. 2016, 59, 17, 8134-8140.

* cited by examiner

*Primary Examiner* — Clinton A Brooks
*Assistant Examiner* — Seong Jon Kim
(74) *Attorney, Agent, or Firm* — Fish IP Law, LLP

(57) ABSTRACT

The present invention relates to a process for preparing B-[(7α,17β)-17-hydroxy-7-[9-[(4,4,5,5,5-pentafluoropentyl)sulfinyl]nonyl]estra-1,3,5(10)-trien-3-yl]-boronic acid, also known as Fulvestrant-3-boronic acid or ZB716, whose structure is shown below:

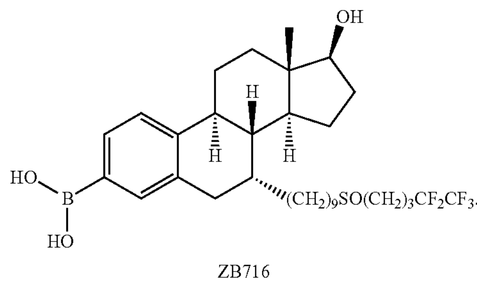

ZB716

9 Claims, No Drawings

PROCESS FOR PREPARING B-[(7α, 17β)-17-HYDROXY-7-[9-[(4,4,5,5,5-PENTAFLUOROPENTYL)SULFINYL] NONYL]ESTRA-1,3,5(10)-TRIEN-3-YL]-BORONIC ACID AND PROCESS INTERMEDIATES

FIELD OF THE INVENTION

The present invention relates to the sector of processes for the synthesis of active ingredients for pharmaceutical use, and in particular to a process for preparing B-[(7α,17β)-17-hydroxy-7-[9-[(4,4,5,5,5-pentafluoropentyl)sulfinyl]nonyl]estra-1,3,5(10)-trien-3-yl]-boronic acid, also known as Fulvestrant-3-boronic acid or ZB716, on an industrial scale. The compound is identified by the CAS Number 1853279-29-4.

The invention further relates to an intermediate of said process.

STATE OF THE ART

ZB716 is useful for the treatment of metastatic breast cancer. The structure of the compound is shown below:

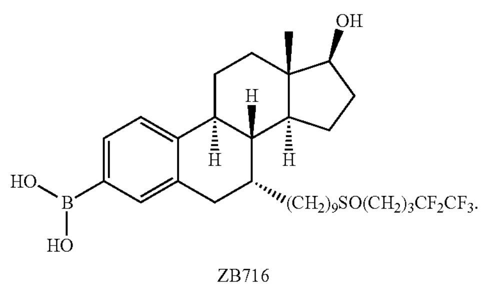

ZB716

The compound is described and claimed in patent EP 3473630 B1 (Compound 29, claim 1) by Xavier University of Louisiana.

The article "Fulvestrant-3 boronic acid (ZB716): an orally bioavailable selective estrogen receptor downregulator (SERD)", J. Liu et al., J. Med. Chem. 2016, 59, 8134-8140, reports an experimental description of the preparation of the compound in question (page 8135, Scheme 1); this synthesis starts from the compound KSM, having the formula shown below:

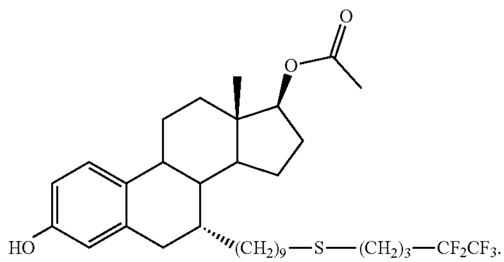

The compound KSM can in turn be obtained by following what is reported in the article "Fulvestrant: from the laboratory to commercial-scale manufacture", E. J. Brazier et al., Org. Process Res. Dev. 2010, 14, 3, 544-552, which describes the synthesis of another active ingredient, Fulvestrant, also currently used for the treatment of metastatic breast cancer.

As can be learned by reading J. Med. Chem. 2016, 59, 8134-8140, the compound ZB716 shows apparent clinical advantages over Fulvestrant that shares with it a large portion of the structure.

In the following FIGURE the structural differences between Fulvestrant and ZB716 are highlighted:

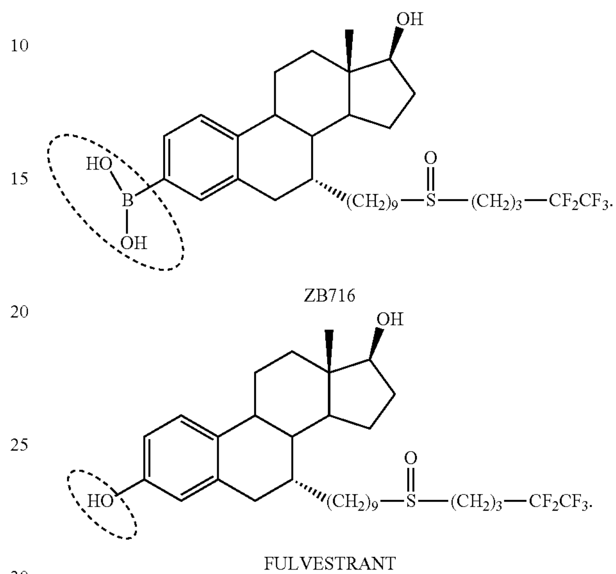

ZB716

FULVESTRANT

The Applicant has been producing Fulvestrant for years but with a different process from that described in the article by E. J. Brazier et al. cited above, described in patent EP 2183267 B1.

This process does not involve the use of intermediate 1 of J. Med. Chem. 2016, 59, 8134-8140, having the following structural formula:

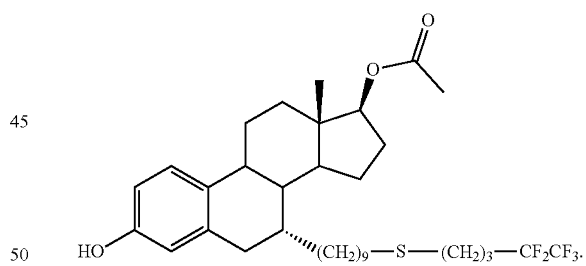

The Applicant has therefore developed a new, industrially applicable, synthetic route for ZB716 which uses Fulvestrant as starting material.

SUMMARY OF THE INVENTION

This object is achieved with the present invention, which in a first aspect relates to a process for the synthesis of ZB716 comprising the following steps:

a) reaction of Fulvestrant, (7α,17β)-7-[9-[(4,4,5,5,5-pentafluoropentyl)sulfinyl]nonyl]-estra-1,3,5(10)-trien-3,17-diol, intermediate N-7 of the process, with a triflating agent, to obtain intermediate N-6, (7α,17β)-7-[9-[(4,4,5,5,5-pentafluoropentyl)sulfinyl]nonyl]-estra-1,3,5(10)-trien-17-ol 3-triflate:

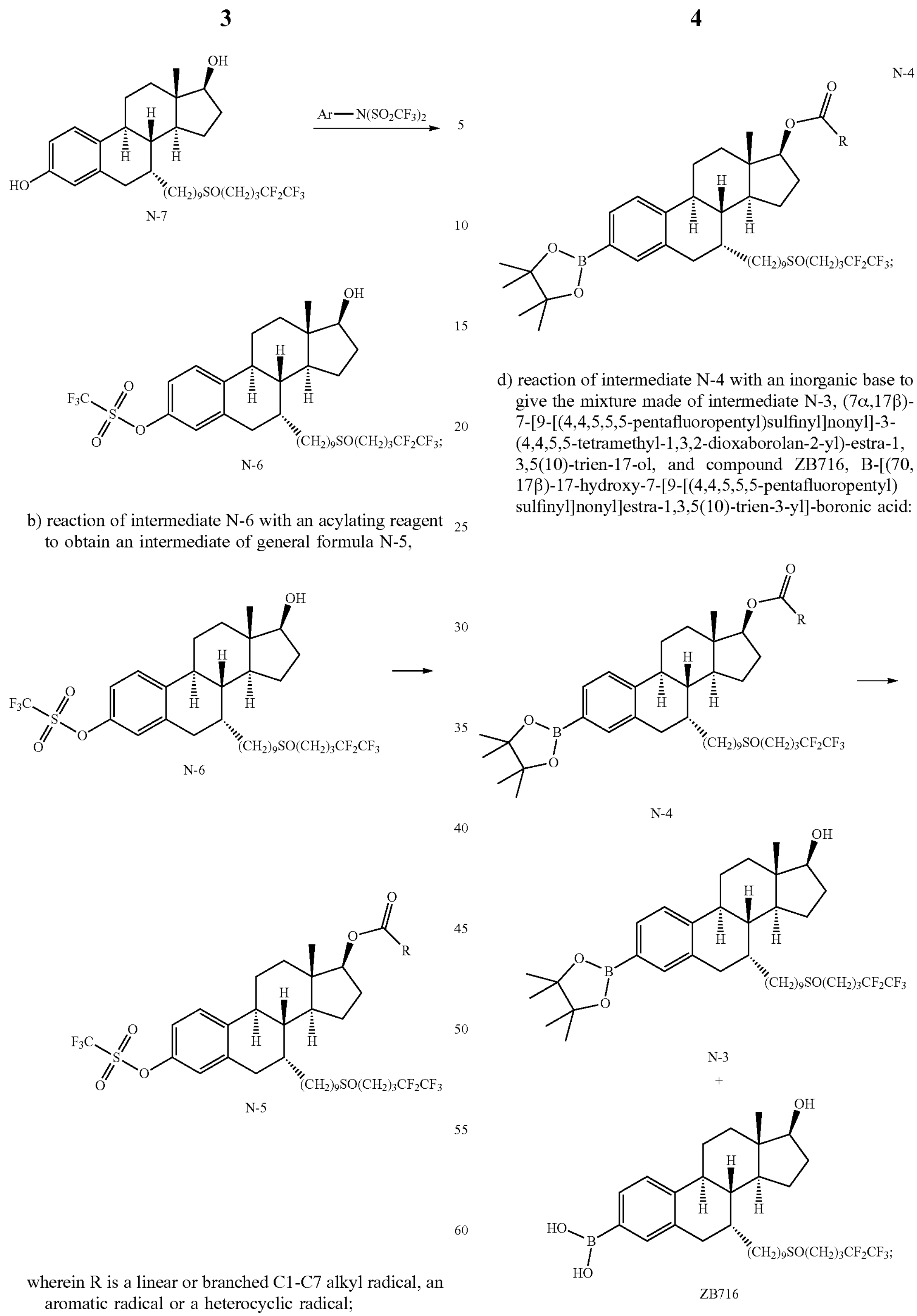

N-7

N-6 b) reaction of intermediate N-6 with an acylating reagent to obtain an intermediate of general formula N-5,

N-6

N-5 wherein R is a linear or branched C1-C7 alkyl radical, an aromatic radical or a heterocyclic radical;

c) reaction of intermediate N-5 with 4,4,4',4',5,5,5',5'-octamethyl-2,2'-bi-1,3,2-dioxaborolane to obtain the intermediate of general formula N-4,

N-4 d) reaction of intermediate N-4 with an inorganic base to give the mixture made of intermediate N-3, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol, and compound ZB716, B-[(70, 17β)-17-hydroxy-7-[9-[(4,4,5,5,5-pentafluoropentyl) sulfinyl]nonyl]estra-1,3,5(10)-trien-3-yl]-boronic acid:

N-4

N-3

+

ZB716 e) reaction of the mixture made of N-3 and compound ZB716 with $KHF_2$ to obtain intermediate N-1, potassium (7α,17β)-7-[9-[(4,4,5,5,5-pentafluoropentyl)sulfinyl]nonyl]-estra-1,3,5(10)-trien-17-ol-3-trifluoroborate:

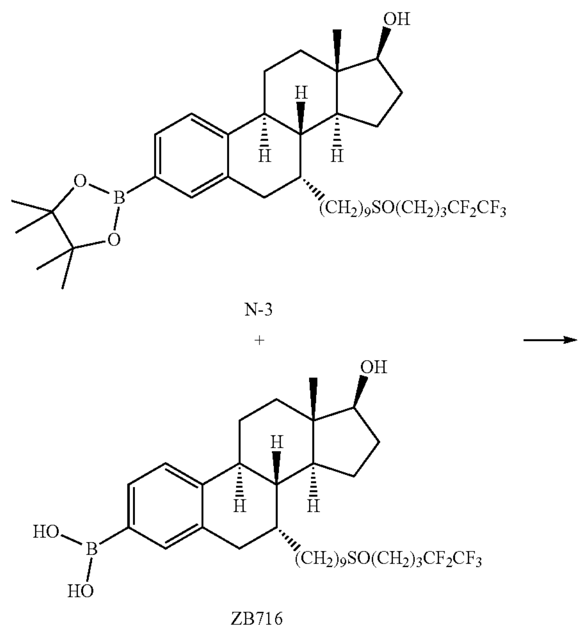

N-3

+

ZB716

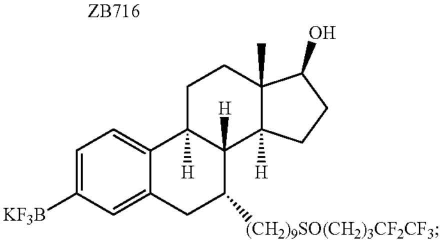

N-1 f) treatment of intermediate N-1 with an inorganic base to give compound ZB716, B-[(7α,17β)-17-hydroxy-7-[9-[(4,4,5,5,5-pentafluoropentyl)sulfinyl]nonyl]estra-1,3,5(10)-trien-3-yl]-boronic acid:

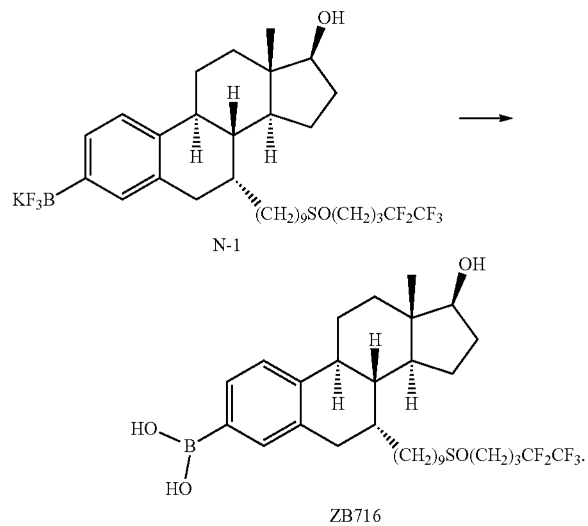

N-1

ZB716

In its second aspect, the invention further relates to compounds of general formula N-5, (7α,17β)-7-[9-[(4,4,5,5,5-pentafluoropentyl)sulfinyl]nonyl]-estra-1,3,5(10)-trien-17-acyloxy 3-triflates, having the structure shown below:

N-5

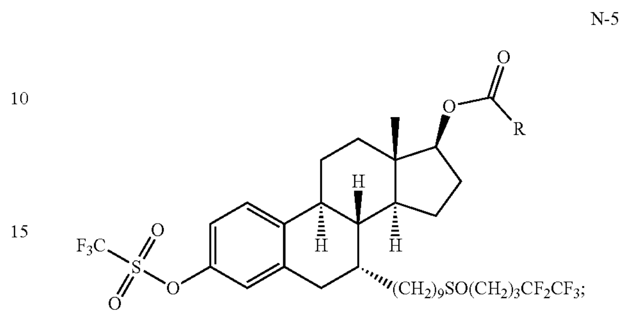

wherein R may be a linear or branched C1-C7 alkyl radical, an aromatic radical or a heterocyclic radical; and to compounds of general formula N-4, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-acyloxy, having the structure shown below:

N-4

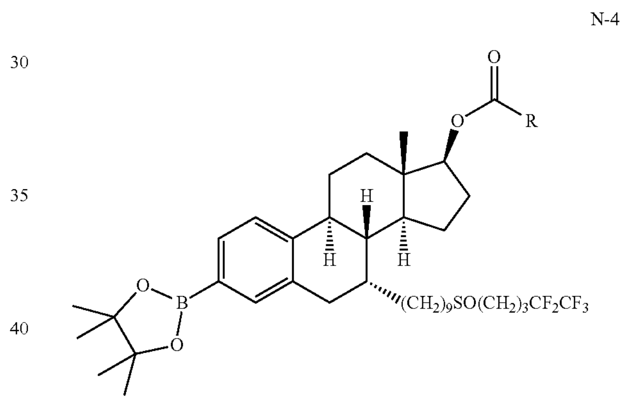

wherein R may be a linear or branched C1-C7 alkyl radical, an aromatic radical or a heterocyclic radical.

DETAILED DESCRIPTION OF THE INVENTION

In its first aspect, the invention relates to a process for the synthesis of ZB716 comprising the steps described below.

In the following description, the ratios between reagents are indicated as w/w, i.e. ratios by weight, unless otherwise specified.

Step a) consists in the reaction of Fulvestrant, (7α,17β)-7-[9-[(4,4,5,5,5-pentafluoropentyl)sulfinyl]nonyl]-estra-1,3,5(10)-trien-3,17-diol, intermediate N-7 of the process, with a triflating agent, to obtain intermediate N-6, (7α,17β)-7-[9-[(4,4,5,5,5-pentafluoropentyl)sulfinyl]nonyl]-estra-1,3,5(10)-trien-3,17-diol 3-triflate:

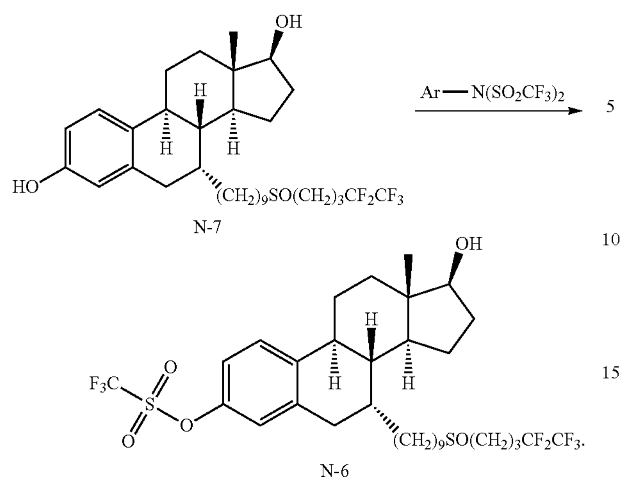

N-7

N-6

Fulvestrant, of a quality suitable for use in the process of the present invention, can be obtained either by following the process described in EP 2183267 B1, or using commercially available Fulvestrant.

Triflation exclusively occurs at the phenolic hydroxy group without having to protect the other hydroxy group present in the molecule, using an aromatic bis(trifluoromethanesulfonimide) of general formula Ar—N(Tf)$_2$ as triflating agent, wherein Ar indicates the aromatic or heteroaromatic radical and the N(Tf)$_2$ group is the radical:

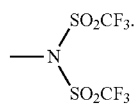

For the purposes of the present invention, the preferred triflating agent is the compound 1,1,1-trifluoro-N-phenyl-N-[(trifluoromethyl)sulfonyl]methanesulfonamide (also commonly referred to as N,N-bis(trifluoromethanesulfonyl) aniline), having the formula shown below:

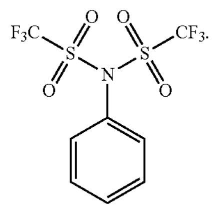 [SMILES: O=S(=O)(N(c1ccccc1)S(=O)(=O)C(F)(F)F)C(F)(F)F]

The triflating agent is used in a (w/w) ratio comprised between 0.30 and 1.20, preferably between 0.6 and 0.9, with respect to intermediate N-7.

The reaction is carried out in dichloromethane (DCM), operating at a temperature comprised between −15 and 40° C., preferably between 0 and 30° C., for a time comprised between 4 and 12 hours, preferably between 6 and 8 hours, in the presence of an organic base selected from triethylamine, diisopropylethylamine, pyridine, 4-(dimethylamino) pyridine, 2,6-lutidine. Triethylamine is preferably used.

Step b) consists in the reaction of intermediate N-6 with an acylating reagent to obtain intermediate N-5, having the general formula shown below:

N-5

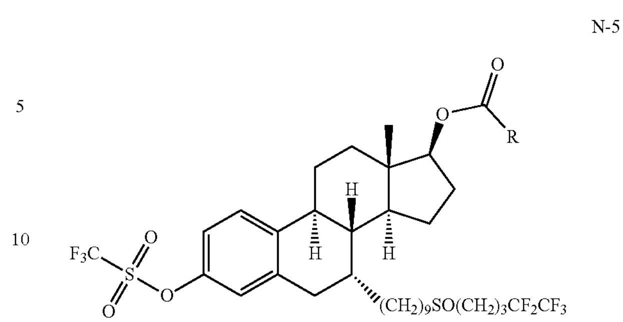

wherein R is a linear or branched C1-C7 alkyl radical, an aromatic radical or a heterocyclic radical. The acylating agent can be selected from those that allow the conversion of the hydroxy group in position 17 of intermediate N-6 into an ester group of general formula —O—CO—R, wherein R has the meaning indicated above.

Preferably the acylating agent is an acetylating agent (R=$-CH_3$); in this case, in step b), the intermediate N-5' (7α,17β)-7-[9-[(4,4,5,5,5-pentafluoropentyl)sulfinyl] nonyl]-estra-1,3,5(10)-trien-17-acetate 3-triflate is obtained:

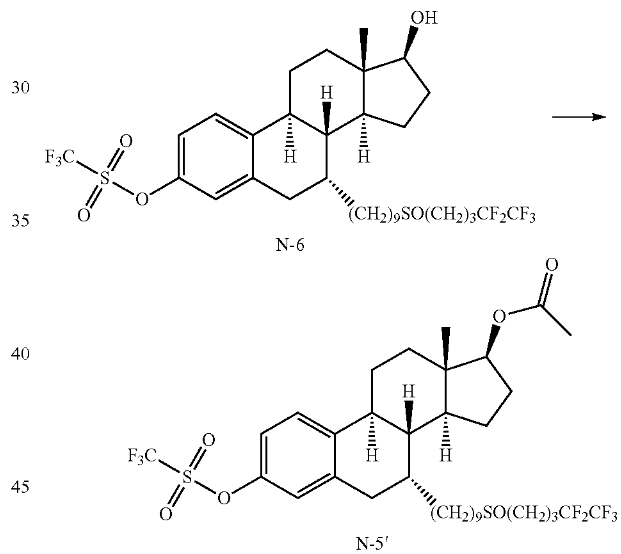

N-6

N-5'

Said conversion can be obtained with procedures known to those skilled in the art, for example by following the instructions provided in the book "Esterification: Methods, Reactions, and Applications" edited by J. Otera and J. Nishikido, second edition, 2010 (Wiley-VCH).

The acetylating reagent is preferably selected from acetic acid, acetyl chloride, acetyl bromide; more preferably acetic anhydride is used.

The reaction occurs in the presence of a catalyst such as 4-DMAP (4-dimethylamino pyridine) and DCC (dicyclohexylcarbodiimide); 4-DMAP is preferably used in the presence of N,N-diisopropylamine, N,N-diisopropylethylamine, triethylamine or, preferably, pyridine. If pyridine is used, this also acts as a solvent for the reaction.

The reaction temperature is comprised between 5 and 40° C., preferably between 20 and 30° C.

The reaction time is comprised between 30 minutes and 6 hours, preferably between 1 and 3 hours.

The molar ration between intermediate N-6 and the acylating agent is comprised between 1 and 3.5, preferably between 2 and 3.

In the preferred case in which acetic anhydride is used, the w/w ratio between intermediate N-6 and the acetylating agent is comprised between 0.20 and 0.50, preferably between 0.25 and 0.40.

Step c) consists in the reaction of intermediate N-5 with 4,4,4',4',5,5,5',5'-octamethyl-2,2'-bi-1,3,2-dioxaborolane, compound having the formula below

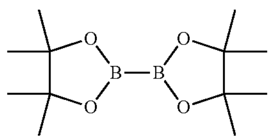

to obtain the intermediate of general formula N-4,

N-4

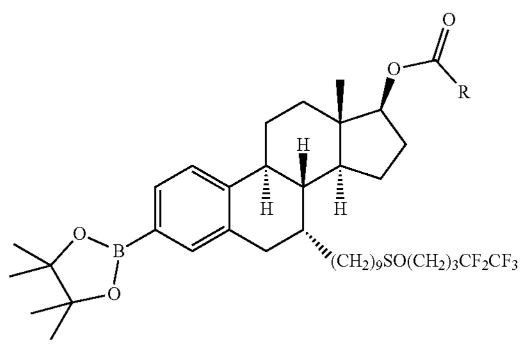

wherein R has the meaning indicated above.

In the preferred case of the invention, R═—$CH_3$, the compound (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-acetate, N-4', is obtained:

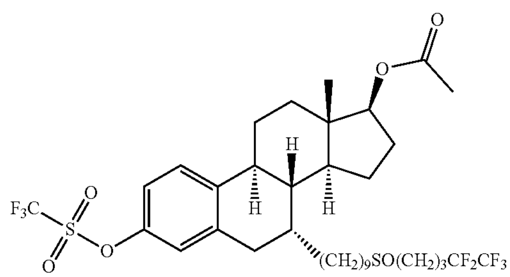

N-5'

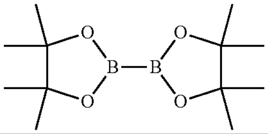

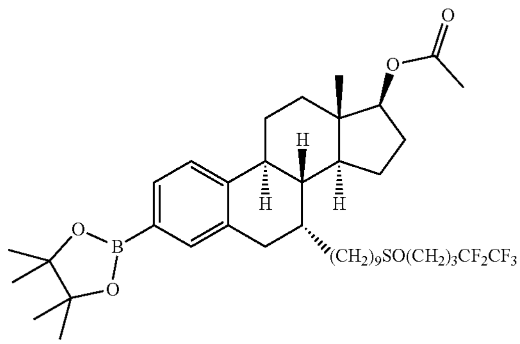

N-4'

The compound 4,4,4',4',5,5,5',5'-octamethyl-2,2'-bi-1,3,2-dioxaborolane, also referred to by the common name of bis(pinacolato)diboron, is normally commercially available.

Bis(pinacolato)diboron is used in a molar ratio comprised between 1 and 3, preferably between 1 and 2, with respect to intermediate N-5.

In the preferred case, R═—$CH_3$, bis(pinacolato)diboron is used in a (w/w) ratio comprised between 0.35 and 0.65, preferably between 0.40 and 0.55, with respect to intermediate N-5'.

The reaction is carried out in acetonitrile operating under the following conditions:

- a temperature comprised between 40 and 90° C., preferably between 35 and 75° C.;
- a time comprised between 0.5 and 6 hours, preferably between 1 and 3 hours;
- in the presence of a compound of palladium(II) such as palladium(II) acetate, palladium(II) chloride, or organometallic compounds comprising palladium(II), such as dichlorobis[cyclohexyldi(1-piperidinyl)phosphine]palladium(II) or diclorobis[tri(1-piperidinyl)phosphine]palladium(II);
- in the presence of a phosphine such as tricyclohexylphosphine, diphenyl(p-tolyl)phosphine, tris(4-fluorophenyl)phosphine, tris(trimethylsilyl)phosphine, tris(1-pyrrolidinyl)phosphine, dicyclohexyl(ethyl)phosphine or tert-butylchloro(methyl)phosphine;
- and in the presence of a base such as potassium or sodium acetate, or potassium or sodium methylate.

Preferably the reaction is carried out using potassium methylate, palladium(II) acetate and tricyclohexylphosphine.

Step d) consists in the reaction of intermediate N-4 with an inorganic base to give the mixture made of intermediate N-3, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol, and compound ZB716, B-[(7α, 17β)-17-hydroxy-7-[9-[(4,4,5,5,5-pentafluoropentyl) sulfinyl]nonyl]estra-1,3,5(10)-trien-3-yl]-boronic acid:

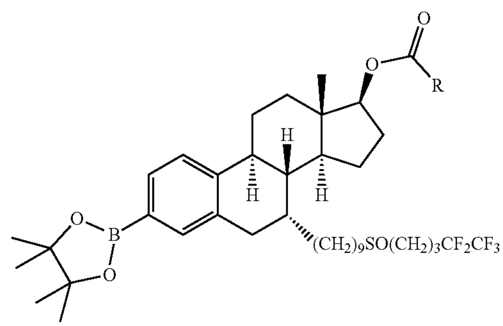

N-4

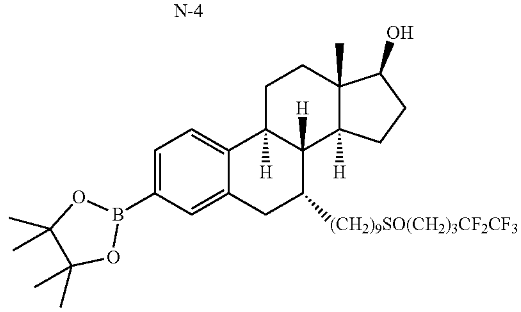

N-3

+

-continued

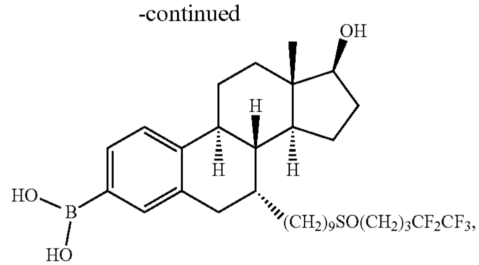

ZB716 wherein R has the meaning indicated above.

In the preferred case of the invention, in which R=—$CH_3$, the same mixture (N-3 and ZB716) obtained in the general case, where R has one of the meanings indicated above, is obtained in this step.

NaOH, KOH, LiOH, anhydrous or in hydrated forms thereof, can be used as inorganic bases. NaOH is preferably used.

The solvent used is a ketone such as acetone, MIBK (methyl isobutyl ketone), MEK (methyl ethyl ketone), cyclohexanone, 3-pentanone; acetone is preferably used.

The base is added to the reaction as an aqueous solution.

The reaction is carried out at a temperature comprised between 1 and 24 hours, preferably between 4 and 12 hours.

The reaction temperature is comprised between 10 and 56° C., preferably between 15 and 40° C.

Step e) consists in the reaction of the mixture of N-3 and ZB716 with $KHF_2$ to obtain intermediate N-1, potassium (7α,17β)-7-[9-[(4,4,5,5,5-pentafluoropentyl)sulfinyl] nonyl]-estra-1,3,5(10)-trien-17-ol-3-trifluoroborate:

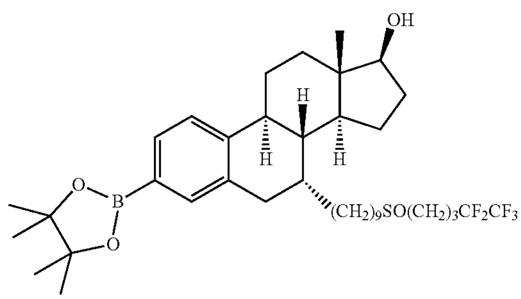

N-3

+

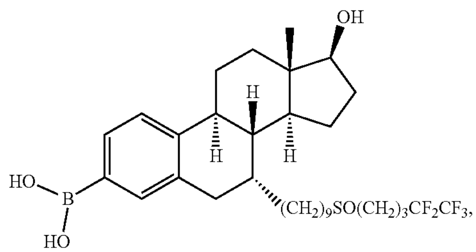

ZB716

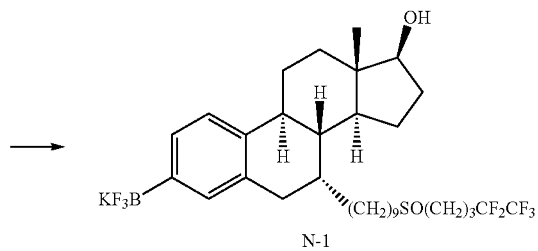

N-1

The compound potassium hydrogen difluoride, $KHF_2$, also referred to by the common name of potassium bifluoride, is normally commercially available.

Its use is also known, as reported in the article "Potassium Organotrifluoroborates: New Perspectives in Organic Synthesis", S. Darses et al., *Chem. Rev.* 2008 (108) 1, pages 288-325.

Potassium bifluoride, $KHF_2$, is used in a (w/w) ratio comprised between 0.45 and 0.75, preferably between 0.55 and 0.70, with respect to the mixture of compound ZB716 and intermediate N-3.

The reaction is carried out in a solvent selected from ethanol, methanol, isopropanol, tert-butanol, acetone, tetrahydrofuran (THF) and acetonitrile and mixtures thereof, anhydrous or in a mixture with water.

Preferred operating conditions are aqueous acetone at a temperature comprised between 10 and 40° C., preferably between 15 e 35° C., for a time comprised between 30 minutes and 4 hours, preferably between 45 minutes and 2 hours.

Finally, in step f) of the process, intermediate N-1 is reacted to give the compound ZB716, B-[(7α,17β)-17-hydroxy-7-[9-[(4,4,5,5,5-pentafluoropentyl)sulfinyl]nonyl]estra-1,3,5(10)-trien-3-yl]-boronic acid:

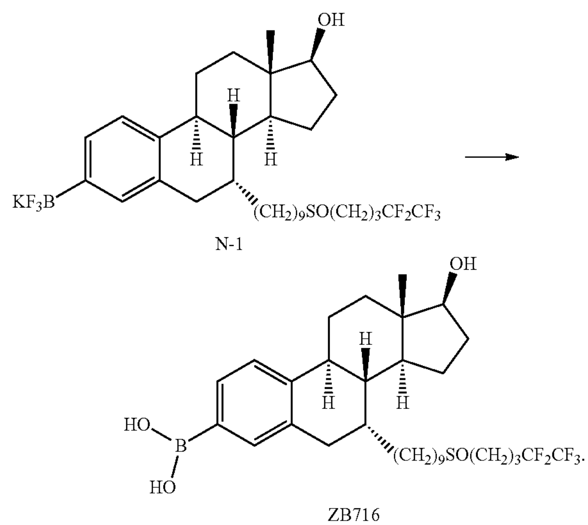

N-1

ZB716

Alkali metal hydroxides, carbonates (lithium, sodium or potassium carbonate), or bicarbonates (sodium and potassium) can be used as reagents.

When using hydroxides, lithium hydroxide hydrate, potassium hydroxide and sodium hydroxide can be used.

Lithium hydroxide monohydrate is preferably used.

When using lithium hydroxide monohydrate, the reagent is used in a (w/w) ratio comprised between 0.1 and 1.5, preferably between 0.15 and 1.0, with respect to intermediate N-1.

The reaction is carried out using a mixture of water with an organic solvent, such as methanol, ethanol, isopropanol, THF, acetonitrile, acetone, isopropyl acetate or ethyl acetate (AcOEt), as solvent.

Preferred reaction conditions are the use of aqueous AcOEt, a temperature comprised between 10 and 45° C., preferably between 20 and 30° C., and a reaction time comprised between 4 and 12 hours, preferably between 5 and 8 hours.

In its second aspect, the invention relates to the compounds having the following general formulas:

(7α,17β)-7-[9-[(4,4,5,5,5-pentafluoropentyl)sulfinyl]nonyl]-estra-1,3,5(10)-trien-17-acyloxy 3-triflate

N-5

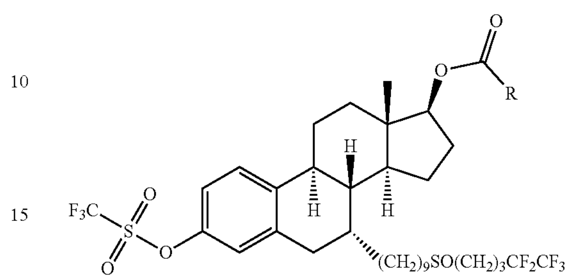

wherein R may be a linear or branched C1-C7 alkyl radical, an aromatic radical or a heterocyclic radical; and (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-acyloxy:

N-4

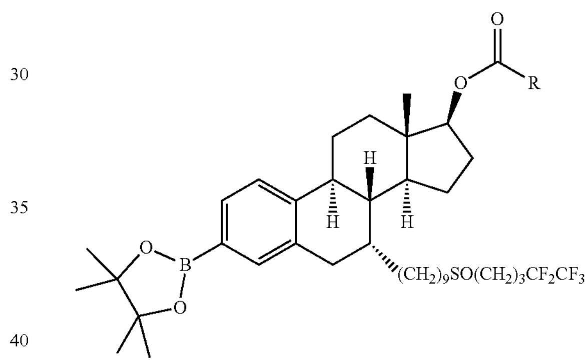

wherein R may be a linear or branched C1-C7 alkyl radical, an aromatic radical or a heterocyclic radical.

The invention will be further illustrated by the following examples.

Instruments, Methods and Experimental Conditions

NMR:

NMR spectrometer JEOL 400 YH (400 MHz); Software JEOL Delta v5.1.1;

Spectra recorded in deuterated solvents such as: Chloroform-d, D 99.8%, containing 0.1% (v/v) tetramethylsilane (TMS) as internal standard; and Chloroform-d, "100%", D 99.96%, containing 0.03% (v/v) TMS, and DMSO-$d_6$.

MS 1:

Instrument: DSQ-trace Thermofisher

Sample introduction—direct exposure probe (dep)

Chemical ionization (CI) with methane

Methane pressure: 2.2 psi

Source Temperature: 200° C.

MS 2:

Instrument: Waters Acquity UPLC QDa Detector

Electrospray ionization (ESI) with formic acid

Source Temperature: 120° C.

UPLC:

Chromatographic System: Waters Acquity UPLC; Detector: Acquity UPLC PDA and λ Detector Chromatographic Conditions:

Column: Acquity UPLC BEH C18 1.7 μm, 2.1×50 mm
Flow Rate: 0.5 mL/min
Detector: UV 225 nm
Injection Volume: 1 μL
Temperature: 35° C.
Mobile phase A: $H_2O$+0.01% formic acid (FA)
Mobile phase B: Acetonitrile+0.01% formic acid (FA)

| TEMPO (MIN.) | MOBILE PHASE A (V/V) | MOBILE PHASE B (V/V) |
|---|---|---|
| 0.00 | 70 | 30 |
| 0.00-1.00 | 70 | 30 |
| 1.00-5.00 | 10 | 90 |
| 5.00-6.00 | 10 | 90 |
| 6.00-9.50 | 0 | 100 |
| 9.50-9.60 | 70 | 30 |
| 9.60-10.50 | 70 | 30 |

TLC

MERCK: TLC silica gel 60 $F_{254}$ Aluminium sheets 20×20 cm, cod. 1.0554.0001.

TLC Stains

Cerium phosphomolybdate: 25 g of phosphomolybdic acid and 10 g cerium (IV)sulfate are dissolved in 600 mL of $H_2O$. 60 mL of 98% $H_2SO_4$ are added and brought to 1 L with $H_2O$. The plate is impregnated with the solution and then heated until the products are detected.

Notes

The water used in the experimental descriptions is to be intended as pure water, unless otherwise indicated.

The organic solvents used in the experimental descriptions are to be intended of "technical" grade, unless otherwise indicated.

The reagents and catalysts used in the experimental descriptions are to be intended of commercial quality, unless otherwise indicated.

Example 1

This example is representative of step a) of the process of the invention.

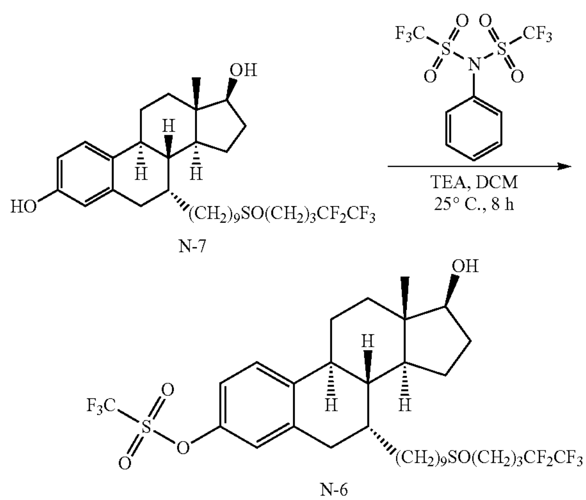

N-7

N-6

A flask is charged with 20 g of Fulvestrant (compound N-7), 200 mL of dichloromethane e 13.7 mL of triethylamine (TEA).

The mixture is cooled to 5° C. and a solution of N,N-bis (trifluoromethanesulfonyl) aniline (16.5 g) dissolved in 70 mL of dichloromethane is added dropwise in about 15 minutes. It is brought to 25° C. and kept under stirring for 8 hours.

Once the reaction is complete (UPLC monitoring), the solvent is concentrated by distilling under reduced pressure at 45° C. until a volume of 100 mL is obtained.

The residue is washed three times with a 1M sodium hydroxide aqueous solution (3×300 mL) and concentrated under reduced pressure at 45° C. obtaining 22 g of intermediate N-6 (oil) that is reacted as such in the subsequent reaction.

The Fulvestrant used as the starting reagent of the method, subjected to $^1$H-NMR and Ms analysis, shows the following analytical data:

$^1$H-NMR (400 MHz, DMSO-d6): 8.99 (s, 1H); 7.04 (d, 1H, J=8.4 Hz); 6.49 (d, 1H, J=8.0 Hz); 6.41 (s, 1H); 4.50 (s, 1H); 3.54-3.52 (m, 1H); 2.76-0.71 (m, 38H); 0.66 (s, 3H).

The $^1$H-NMR signals at 8.99 ppm and 4.50 ppm (attributable to the mobile protons in position 3 and 17) disappear after deuteration of the sample with $D_2O$.

Massa (ESI): m/z=629 [$M^+$+1+22]; 607 [$M^+$+1]; 589 [$M^+$+1−$H_2O$].

The obtained intermediate N-6, submitted to $^1$H-NMR and Ms analysis, shows the following analytical data:

$^1$H-NMR (400 MHz, DMSO-d6): $^1$H-NMR (400 MHz, DMSO-d6): 7.42 (d, 1H, J=8.8 Hz); 7.15-7.12 (m, 2H); 4.50 (d, 1H, J=4.4 Hz); 3.53-3.48 (m, 1H); 2.82-0.80 (m, 38H); 0.63 (s, 3H).

The $^1$H-NMR signal at 4.50 ppm (attributable to the mobile proton in position 3) disappears after deuteration of the sample with $D_2O$.

Mass (ESI$^+$): m/z=761 [$M^+$+1+22]; 739 [$M^+$+1]; 619 [$M^+$+1−$HCF_2CF_3$].

Example 2

This example is representative of step b) of the process of the invention.

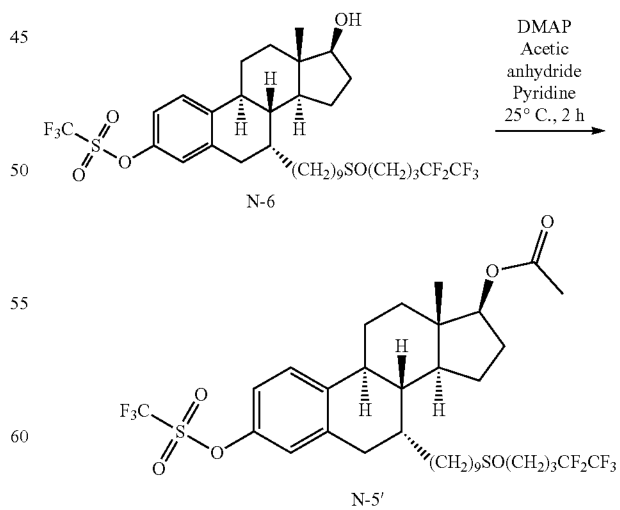

N-6

N-5′

A flask is charged with 1 g of intermediate N-6, obtained according to the procedure described in the previous example, and 14 mL of pyridine.

10 mg of 4-dimethylaminopyridine are added, and then 0.3 mL of acetic anhydride are added dropwise while keeping the temperature below 30° C.

The mixture is kept under stirring at 25° C. for 2 hours.

The reaction is monitored by TLC analysis, under the following conditions: TLC plate: silica gel on alumina; starting substrate (intermediate N-6) dissolved in dichloromethane; reaction mixture quenched in 1M HCl and extracted with ethyl acetate, the organic layer is spotted; eluent: EtOAc/heptane, 7:3; stain: cerium phosphomolybdate.

The reaction mixture is poured into 12 mL of 1M hydrochloric acid pre-cooled to 5° C.

The layers are separated, and the organic layer is washed twice with 1M hydrochloric acid (2×10 mL) and then with water (2×10 mL).

It is concentrated under reduced pressure at 45° C. obtaining 1.2 g of intermediate N-5' (oil).

The intermediate N-5' obtained, subjected to 1H-NMR and Ms analysis, shows the following analytical data:

$^1$H-NMR (400 MHz, DMSO-d6): 7.40 (d, 1H, J=8.8 Hz); 7.13-7.10 (m, 2H); 4.59 (t, 1H, J=8.4 Hz); 2.83-0.82 (m, 38H); 1.95 (s, 3H); 0.73 (s, 3H).

Massa (ESI$^+$): m/z=781 [M$^+$+1].

Example 3

This example is representative of step c) of the process of the invention.

A flask is charged with intermediate N-5' (1.2 g), obtained according to the procedure described in the previous example, and 24 mL of acetonitrile. The mixture is kept under stirring at 25° C. for 10 minutes. 0.6 g of bis (pinacolato)diboron, 0.4 g of potassium methylate, 0.1 g of tricyclohexylphosphine and 45 mg of palladium acetate are added to the solution. It is heated to 60° C. for 1 hour.

Once the reaction is complete (UPLC monitoring), the reaction mixture is filtered, and the filtration liquid is concentrated under reduced pressure at 45° C. to obtain 1 g of crude intermediate N-4'.

The product is purified by chromatographic column on silica gel, eluting with a 40:60 heptane/isopropyl acetate mixture. The solvent is concentrated under reduced pressure at 45° C. obtaining 900 mg of intermediate N-4' (oil).

The intermediate N-4' is analysed by 1H-NMR and mass spectroscopy.

$^1$H-NMR (400 MHz, DMSO-$d_6$): 7.35 (d, 1H, J=8.0 Hz); 7.31 (s, 1H); 7.28 (d, 1H, J=8.4 Hz); 4.59 (t, 1H, J=8.2 Hz); 2.83-0.77 (m, 50H); 1.96 (s, 3H); 0.73 (s, 3H).

Massa (ESI$^+$): m/z=759 [M$^+$+1].

Example 4

This example is representative of step d) of the process of the invention.

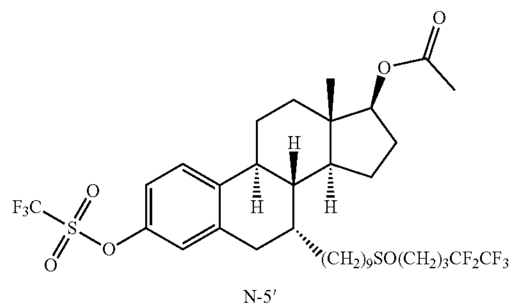

N-5'

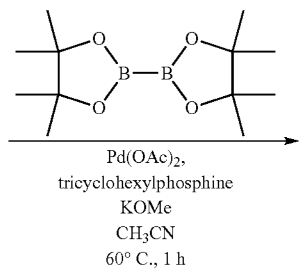

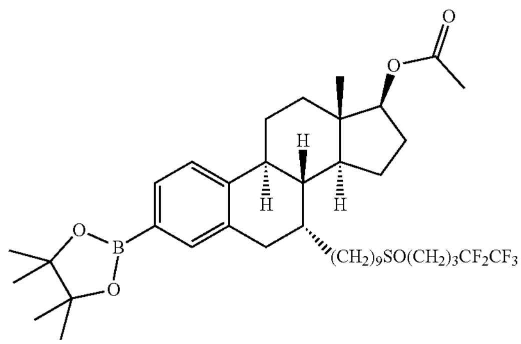

N-4'

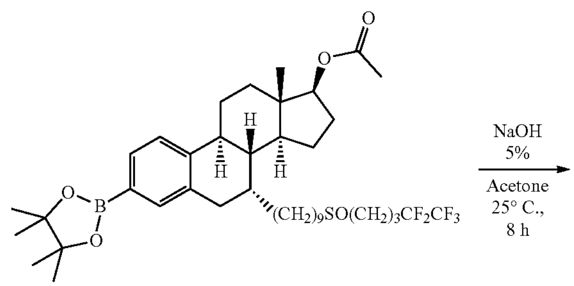

N-4′

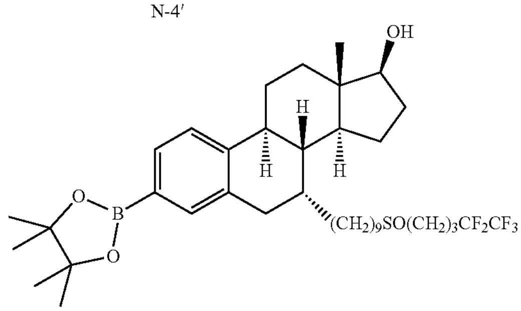

N-3

+

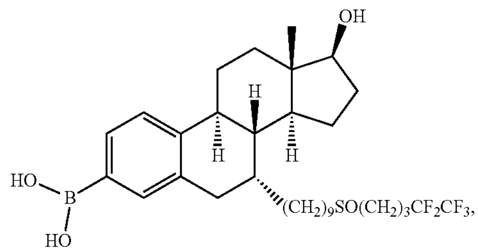

ZB716

A flask is charged with intermediate N-4' (900 mg), obtained according to the procedure described in the previous example, and 9 mL of acetone.

A 5% sodium hydroxide aqueous solution (9 mL) is added to the mixture and the mixture is stirred at 25° C. for 8 hours.

The reaction is monitored by TLC analysis, under the following conditions: TLC plate: silica gel on alumina; starting substrate (intermediate N-4') dissolved in dichloromethane; reaction mixture quenched in 1M HCl and extracted with ethyl acetate, the organic layer is spotted; eluent: ethyl acetate; stain: cerium phosphomolybdate.

Once the reaction is complete, it is cooled to 5° C. and neutralised with a 37% hydrochloric acid aqueous solution. The solvent is removed under reduced pressure at 45° C. and the residue is extracted with 10 mL of ethyl acetate.

The layers are separated, and the organic layer is washed twice with water (2×10 mL).

It is concentrated under reduced pressure at 45° C. obtaining 700 mg of yellow oil.

The intermediate obtained, analysed by UPLC analysis, shows the formation of a mixture of intermediate N-3 and ZB716, whose peak areas in the UPLC chromatogram are in a 47:53 ratio.

Example 5

This example is representative of step e) of the process of the invention.

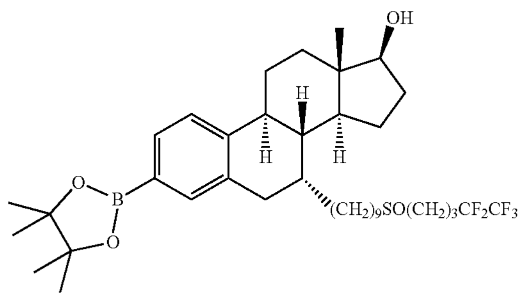

N-3

+

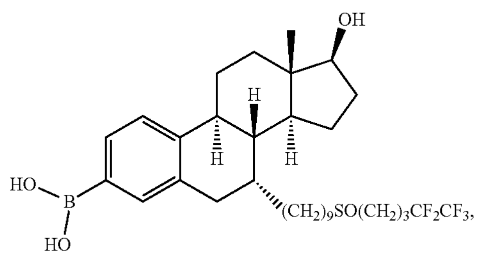

ZB716

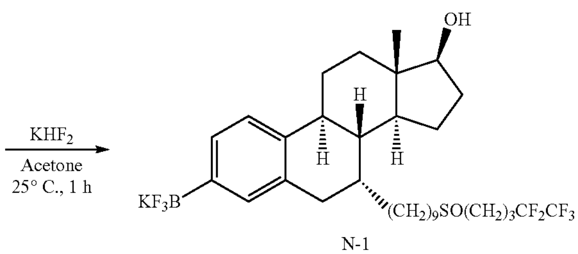

N-1

A flask is charged with the mixture of intermediate N-3 and compound ZB716 (700 mg) obtained according to the procedure described in the previous example, and 2.8 mL of acetone.

A potassium bifluoride solution (430 mg) dissolved in water (1.2 mL) is added to the mixture and kept under stirring at 25° C. for 1 hour (the reaction is monitored by UPLC analysis).

Once the reaction in complete, the solvent is removed under reduced pressure at 45° C. and the residue is extracted with ethyl acetate (10 mL).

The inorganic salts present are filtered, and the filtration liquid is concentrated under reduced pressure at 45° C. obtaining 400 mg of crude potassium Fulvestrant 3-trifluoroborate (yellow oil). The residue is taken up with 2 mL of dichloromethane and added dropwise to an ethyl ether solution cooled to 0° C. The suspension is kept under stirring at 25° C. for 1 hour. The solid is filtered washing with chilled ethyl ether. The solid is resuspended with ethyl ether (4 mL), the suspension is kept under stirring at 25° C. for 1 hour, and the solid is filtered washing with ethyl ether. The solid is dried under reduced pressure at 45° C. obtaining 400 mg of white solid.

Intermediate N-1 is analysed by 1H-NMR and mass spectroscopy.

$^{1}$H-NMR (400 MHz, DMSO-$d_6$): 7.03 (d, 1H, J=8.0 Hz); 6.98 (d, 1H, J=9.1 Hz); 6.97 (s, 1H); 4.51 (d, 1H, J=4.8 Hz); 3.55-3.51 (m, 1H); 2.81-0.71 (m, 38H); 0.67 (s, 3H).

The $^{1}$H-NMR signal at 4.51 ppm disappears after deuteration of the sample with $D_2O$.

$^{19}$F-NMR (400 MHz, DMSO-$d_6$): −84.5 (s, $CF_3$); −117.1 (s, $CF_2$); −138.52 (s, $BF_3$).

Mass (ESI$^-$): m/z=657.

Example 6

This example is representative of step f) of the process of the invention.

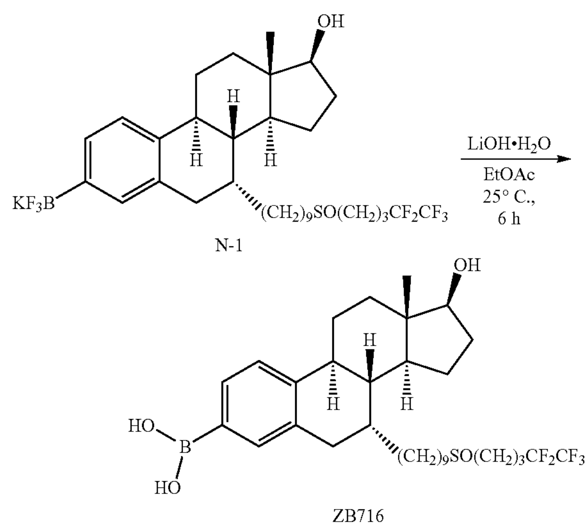

A flask is charged with 300 mg of intermediate N-1 and 4.2 mL of ethyl acetate.

A solution of lithium hydroxide monohydrate (63 mg) in water (2.1 mL) is added to the mixture and kept under stirring at 25° C. for 6 hours (the reaction is monitored by $^{1}$H-NMR and $^{19}$F-NMR analysis).

Once the reaction is complete, a saturated ammonium chloride solution (3 mL) is added, the layers are separated, and the aqueous layer is re-extracted with ethyl acetate. The organic layer is washed with a saturated sodium chloride aqueous solution and concentrated under reduced pressure at 45° C. obtaining 250 mg of crude ZB716 (yellow solid).

The crude product is dissolved in the smallest amount of tetrahydrofuran and crystallized with acetonitrile.

The solid is dried under reduced pressure at 45° C. obtaining 200 mg of the desired compound, ZB716, as a white solid whose $^{1}$H-NMR, $^{13}$C-NMR and Ms analytical data coincide with those reported in the literature.

$^{1}$H-NMR (400 MHz, DMSO-$d_6$): 7.68 (s, 2H); 7.50 (d, 1H, J=7.6 Hz); 7.43 (s, 1H); 7.23 (d, 1H, J=7.6 Hz); 4.36 (d, 1H, J=4.4 Hz); 3.56-3.55 (m, 1H); 2.84-2.60 (m, 6H); 2.45-2.25 (m, 4H); 1.94-1.10 (m, 26H); 0.88 (m, 2H); 0.67 (s, 3H).

The $^{1}$H-NMR signals at 7.68 ppm and 4.36 ppm disappear after deuteration of the sample with $D_2O$.

$^{19}$F-NMR (400 MHz, DMSO-$d_6$): −84.5 (s, $CF_3$); −117.1 (s, $CF_2$).

$^{13}$C-NMR (400 MHz, DMSO-$d_6$): 141.8; 136.4; 134.2; 131.9; 125.3; 80.6; 51.7; 49.9; 46.7; 43.5; 42.1; 39.1; 37.4; 34.7; 33.3; 30.4; 29.8; 29.5; 29.3; 29.1; 29.0; 28.6; 28.0; 27.3; 25.6; 22.8; 22.5; 14.6; 11.8.

Mass (ESI$^+$): m/z=657 [$M^+$+1+22]; 635 [$M^+$+1]; 617 [$M^+$+1−$H_2O$].

What is claimed is:

1. A process for the synthesis of B-[(7α,17β)-17-hydroxy-7-[9-[(4,4,5,5,5-pentafluoropentyl)sulfinyl]nonyl]estra-1,3,5 (10)-trien-3-yl]-boronic acid (compound ZB716), comprising the following steps:

a) reaction of Fulvestrant, (7α,17β)-7-[9-[(4,4,5,5,5-pentafluoropentyl)sulfinyl]nonyl]-estra-1,3,5 (10)-trien-3,17-diol, intermediate N-7 of the process, with a triflating agent, to obtain intermediate N-6, (7α, 17β)-7-[9-[(4,4,5,5,5-pentafluoropentyl)sulfinyl]nonyl]-estra-1,3,5 (10)-trien-17-ol 3-triflate:

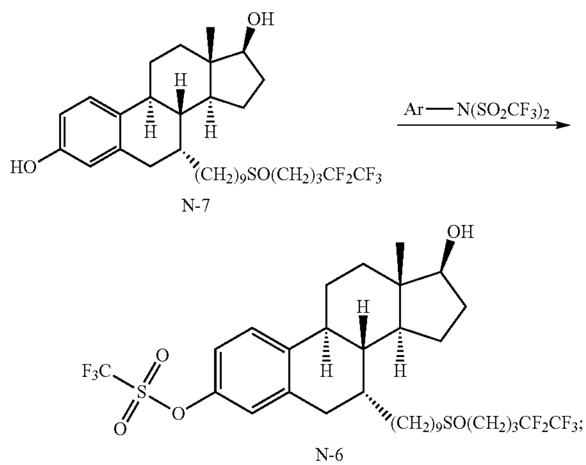

b) reaction of intermediate N-6 with an acylating reagent to obtain an intermediate of general formula N-5,

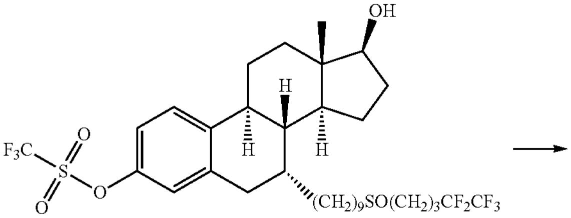

N-6

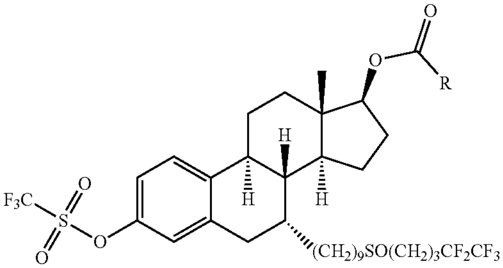

N-5 wherein R is selected from a linear or branched C1-C7 alkyl radical, an aromatic radical and a heterocyclic radical;

c) reaction of intermediate N-5 with 4,4,4',4',5,5,5',5'-octamethyl-2,2'-bi-1,3,2-dioxaborolane to obtain the intermediate of general formula N-4,

N-4

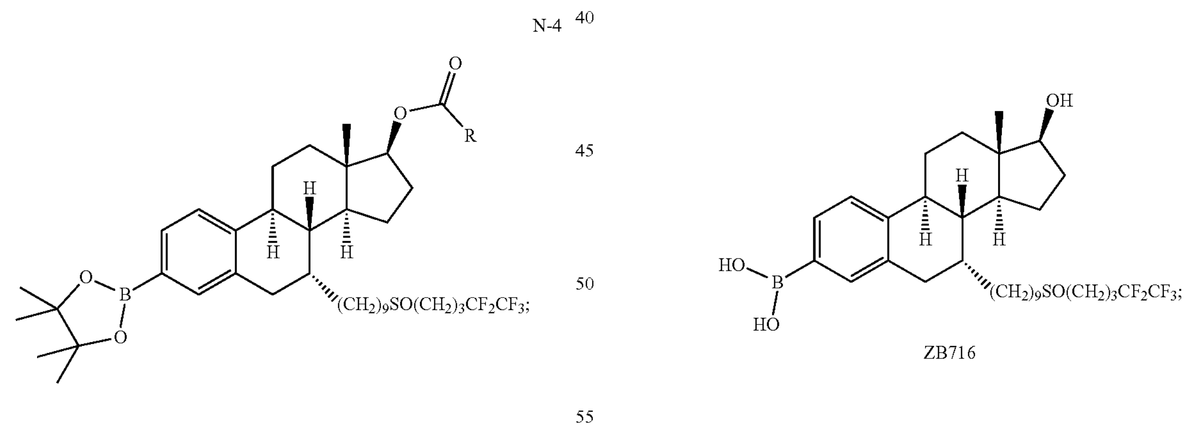

ZB716 d) reaction of intermediate N-4 with an inorganic base to give the mixture made of intermediate N-3, (7α, 17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5 (10)-trien-17-ol, and compound ZB716, B-[(7α, 17β)-17-hydroxy-7-[9-[(4,4,5,5,5-pentafluoropentyl) sulfinyl]nonyl]estra-1,3,5 (10)-trien-3-yl]-boronic acid:

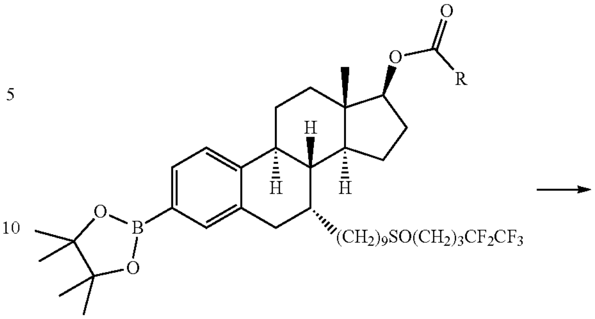

N-4

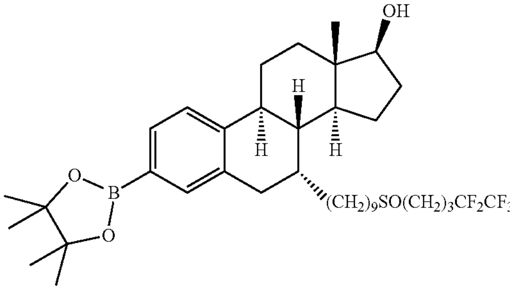

N-3

+ e) reaction of the mixture made of intermediate N-3 and compound ZB716 with $KHF_2$ to obtain intermediate N-1, potassium (7α,17β)-7-[9-[(4,4,5,5,5-pentafluoropentyl)sulfinyl]nonyl]-estra-1,3,5 (10)-trien-17-ol-3-trifluoroborate:

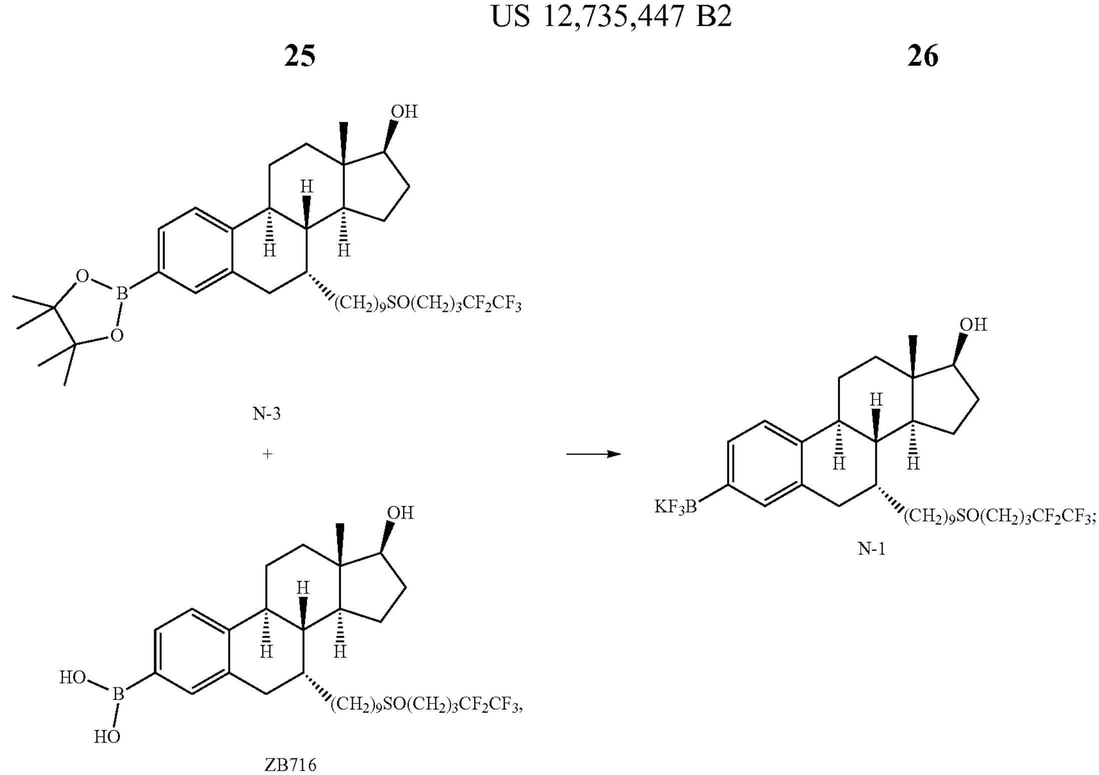

N-3

+

ZB716

N-1 f) treatment of intermediate N-1 with an inorganic base to give compound ZB716, B-[(7α, 17β)-17-hydroxy-7-[9-[(4,4,5,5,5-pentafluoropentyl)sulfinyl]nonyl]estra-1,3,5 (10)-trien-3-yl]-boronic acid:

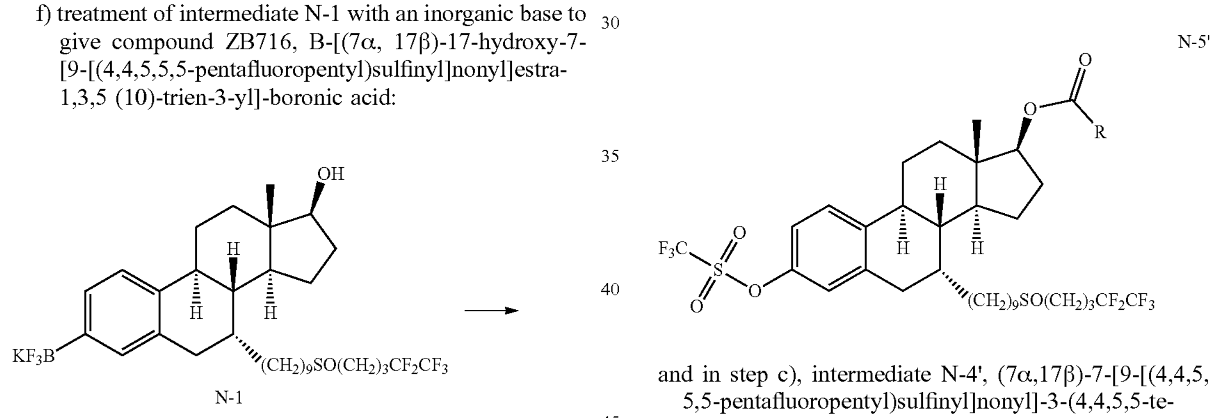

N-1

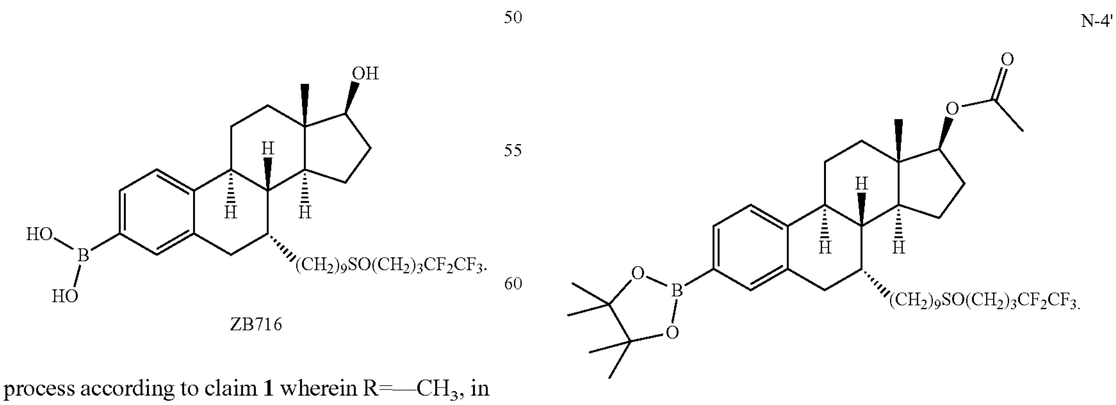

ZB716

2. The process according to claim 1 wherein R=—$CH_3$, in step b) is produced intermediate N-5', (7α,17β)-7-[9-[(4,4,5,5,5-pentafluoropentyl)sulfinyl]nonyl]-estra-1,3,5 (10)-trien-17-acetate 3-triflate, having the following formula:

N-5' and in step c), intermediate N-4', (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5 (10)-trien-17-acetate is produced, having the following formula:

N-4'

3. The process according to claim 1, wherein in step a) an aromatic bis(trifluoromethanesulfonimide) of general formula Ar—N(Tf)$_2$ is used as triflating agent, wherein Ar indicates the aromatic or heteroaromatic radical and the N(Tf)$_2$ group is the radical:

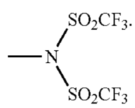

4. The process according to claim 1, wherein said triflating agent is 1,1,1-trifluoro-N-phenyl-N-[(trifluoromethyl)sulfonyl]methanesulfonamide.

5. The process according to claim 1, wherein the acylating agent of step b) is acetic anhydride.

6. A compound (7α, 17β)-7-[9-[(4,4,5,5,5-pentafluoropentyl)sulfinyl]nonyl]-estra-1,3,5 (10)-trien-17-acyloxy 3-triflate, of general formula:

N-5

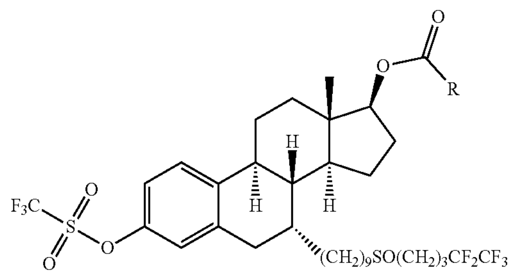

wherein R is selected from a linear or branched C1-C7 alkyl radical, an aromatic radical and a heterocyclic radical.

7. The compound N-5' according to claim 6, wherein R=—$CH_3$

N-5'

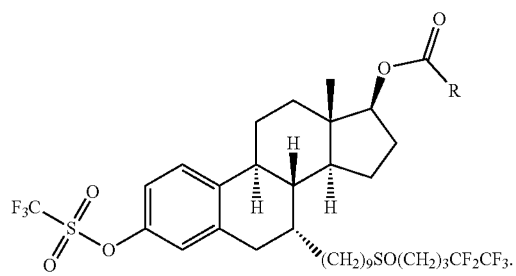

8. The compound (7α, 17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5 (10)-trien-17-acyloxy, of general formula:

N-4

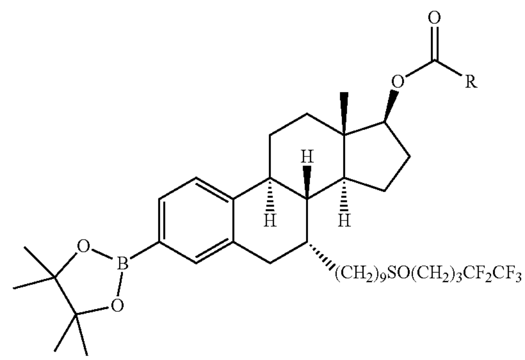

wherein R is selected from a linear or branched C1-C7 alkyl radical, an aromatic radical and a heterocyclic radical.

9. The compound N-4' according to claim 8, wherein R=—$CH_3$

N-4'

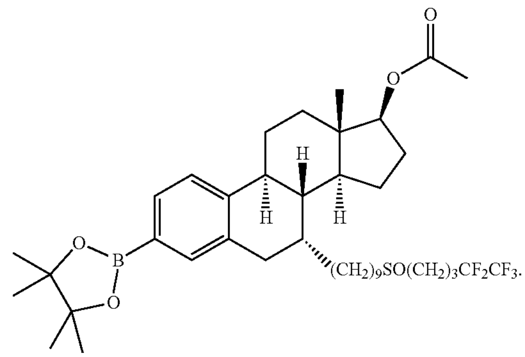

* * * * *